United States Patent [19]
Catani et al.

[11] Patent Number: 5,952,205
[45] Date of Patent: Sep. 14, 1999

[54] PROCESS FOR PROCESSING SUCROSE INTO GLUCOSE AND FRUCTOSE

[75] Inventors: Steven J. Catani, Athens, Ga.; Stephen A. Roth, Gladwyne; Edward J. McGuire, Furlong, both of Pa.; Juan L. Navia, Athens, Ga.

[73] Assignee: Neose Technologies, Inc., Horsham, Pa.

[21] Appl. No.: 09/019,709

[22] Filed: Feb. 6, 1998

[51] Int. Cl.[6] .............................. C12N 9/10; C12P 19/02; C12P 19/04

[52] U.S. Cl. .......................... 435/101; 435/105; 435/193

[58] Field of Search .................................. 435/101, 105, 435/193

[56] References Cited

U.S. PATENT DOCUMENTS

| | | |
|---|---|---|
| 4,133,875 | 1/1979 | Hillman . |
| 4,150,116 | 4/1979 | Taubman et al. . |
| 4,263,052 | 4/1981 | Bichsel et al. . |
| 4,277,563 | 7/1981 | Kerkhoffs . |
| 4,299,677 | 11/1981 | Venkatasubramanian et al. . |
| 4,317,880 | 3/1982 | Heady . |
| 4,335,207 | 6/1982 | Heady . |
| 4,340,673 | 7/1982 | Stoudt et al. . |
| 4,356,262 | 10/1982 | Heady ...................................... 435/101 |
| 4,619,825 | 10/1986 | Eigen et al. . |
| 4,637,835 | 1/1987 | Nagle . |
| 4,681,771 | 7/1987 | Adachi et al. . |
| 4,742,006 | 5/1988 | Bringer et al. . |
| 4,774,183 | 9/1988 | Fan . |
| 5,002,759 | 3/1991 | Gaffar et al. . |
| 5,095,106 | 3/1992 | Gaffar et al. . |
| 5,169,679 | 12/1992 | Palanisamy . |
| 5,314,810 | 5/1994 | Kono et al. . |
| 5,478,732 | 12/1995 | Kunz et al. . |
| 5,524,075 | 6/1996 | Rousseau et al. . |

OTHER PUBLICATIONS

Computer FSTA Abstract 95(07) :B0022 Hang et al "Enzymatic conversion of sucrose to kestose by fungal extracelluar fructosyltransferase" Biotechnology Letters (1995) 17 (3) 295–298.

*Primary Examiner*—Herbert J. Lilling
*Attorney, Agent, or Firm*—Oblon, Spivak, McClelland, Maier & Neustadt, P.C.

[57] ABSTRACT

The present invention relates to a process of preparing commercial quantities of glucose and/or fructose from sucrose, a process of preparing commercial quantities of glucose and a polyfructan from sucrose, a reactor for practicing same, a process of preparing commercial quantities of fructose and a polyglucan from sucrose and a reactor for practicing same.

12 Claims, 4 Drawing Sheets

PROCESS FOR PROCESSING SUCROSE INTO GLUCOSE AND FRUCTOSE

BACKGROUND OF THE INVENTION

1. Field of the Invention

The present invention relates to a process of preparing commercial quantities of glucose and/or fructose from sucrose and a reactor for practicing same. In particular the present invention relates to a process for preparing glucose and/or fructose from sucrose by contacting sucrose with a fructosyltransferase and/or a glucosyltransferase, followed by isolating glucose and a polyfructan, fructose and a polyglucan or both.

2. Description of the Background

Glucose and fructose are saccharides that are found throughout nature, either as monosaccharides or incorporated into polysaccharides. Glucose is used clinically as a fluid and nutrient replenisher, as a carbon source in the culturing of microorganisms and is widely used as a food additive. Fructose is also clinically used as a fluid and nutrient replenisher and widely as a food additive.

Glucose has been prepared commercially from starch (Dean, Gottfried, *Advan. Carbohyd. Chem.* 5, 127 (1950) and by acid hydrolysis of sucrose. Fructose has been prepared by hydrolysis of inulin (Bates et al. Natl.Bur. Std. (U.S.) Circ. C440, 39 (1942)), from dextrose (Cantor, Hobbs U.S. Pat. No. 2,354,664) and enzymatically from sucrose (Koepsell et al. U.S. Pat. No. 2,729,587). In spite of the availability of the starting materials for preparing glucose and fructose, the cost of these materials remains high, relative to the cost of the starting materials. Accordingly, commercial syntheses of both glucose and fructose can be improved.

Inulins are polysaccharides belonging to the polyfructan group and occur in many different plants including, for example, Jerusalem artichokes, dahlia tubers, and chicory roots. Inulins are comprised of $\beta$-2,1-linked fructose chains, linked to an $\alpha$ D-glucoside; they have a linear structure and typically comprise many $\beta$-O-fructofuranose units. The average chain length and molecular weight distribution will depend on both the plant species, the growth phase, and the preparation method. Average chain lengths of 10 to 25 are common, in which case the individual units have about 9 to 24 fructose units.

The properties of an inulin will vary depending on the chain length. Compositions comprising short chain inulins having a degree of polymerization of about 3 to 7 fructose units have been used as reduced calorie sugar substitutes (DE 4,003,140).

Polyglucans are polysacharides of glucose units, typically connected by $\alpha$-1,3, $\alpha$-1,6, $\beta$-1,2, $\beta$-1,3, and $\beta$-1,4 linkages. A class of polyglucans comprised of $\alpha$-1,3 and $\alpha$-1,6 linkages are produced in nature by many oral bacteria flora, such as *S. mutans*, and are believed to assist in the colonization of the oral cavity by these organisms, which produce the disease state of dental caries. The polyglucan based entirely on $\beta$-1,4 linkages is produced by plants, as cellulose. The polyglucan based entirely on $\beta$-1,3 linkages is produced by plants, as callose. Another polyglucan based on random linkages, typically terminating with a sorbitol, is known as polydextrose and is used as a food bulking agent.

Stoudt et al. U.S. Pat. No. 4,340,673 report a modified glucan prepared biosynthetically from a glucosyltransferase, sucrose and an endo $\alpha$-1,3glucan-3-glucanohydrolase for the modification of dental plaque development.

Gaffar et al. U.S. Pat. No. 5,095,106 and U.S. Pat. No. 5,002,759 report an oligosaccharide having at least one fucose moiety or a galactose moiety, said oligosaccharide which is free of digalactose and N-acetlyneuraminyl lactose, for inhibiting adherence of *Streptococcus pyogenes* to pharyngeal and oral mucosa cells.

Taubman et al. U.S. Pat. No. 4,150,116 report that *Strepotcoccus mutan* colonization may be inhibited by immunization with a purified form of a glucosyltranferase.

Eigen et al. U.S. Pat. No. 4,619,825 report plaque inhibition by treatment with a water dispersion of emulsan.

Hillman et al. U.S. Pat. No. 4,133,875 report that an effector strain of *Streptococcus mutans* may be effective to control the incidence and severity of dental caries.

In the area of fructose production Kerkhoffs et al U.S. Pat. No. 4,277,563 report the isolation of fructose by hydrolysis of a polyfructan such as inulin.

Bichsel et al. U.S. Pat. No. 4,263,052 report the production of fructose by hydrolysis of a fructofuranoside such as sucrose and enrichment in fructose by precipitation of a calcium-fructose complex.

Fan et al. U.S. Pat. No. 4,774,183 report that fructose can be isolated from a mixture of fructose and glucose by contacting with a microorganism such as *Pullularia pullulans* which preferentially utilizes glucose.

Bringer et al. U.S. Pat. No. 4,742,006 report the production of fructose from mixtures of fructose and glucose by contacting with a glucose decomposing mutant of *Zymomonas mobilis*.

In the area of glucose production, Nagle et al. U.S. Pat. No. 4,637,835 report the preparation of glucose and other saccharides from an $\alpha$-cellulose using a calcium chloride catalyst and hydrogen ions.

Miyawaki et al. U.S. Pat. No. 5,524,075 report the production of high purity glucose by saccharifying liquefied starch with an enzyme.

Venkatasubramanian et al. U.S. Pat. No. 4,299,677 report the direct separation of fructose and glucose from a mixture of glucose and fructose by ion exchange membranes.

Harada et al. U.S. Pat. No. 5,169,679 report the use of polyfrucans composed mainly of $\beta$-2,1 bonds having a molecular weight of from 2,000 to 20,000,000 as food additives such as, for example, bulking agents or fat substitutes, for producing low calorie foods.

Kurz et al. U.S. Pat. No. 5,478,732 report a method for obtaining intermediate-chain inulins (e.g. a degree of polymerization of 10–12) by treatment of crude inulin suspensions with a hydrolase enzyme. During the enzymatic treatment, short-chain components are degraded to mono- and disaccharides while long-chain inulins are separated off, then converted to a dry form.

Adachi et al. report in U.S. Pat. No. 4,681,771 that when sucrose (G-F) is contacted with an enzyme having fructose transferring activity (hereinafter referred to as a fructosyltransferase), a low caloric, low-cariogenic sweetener composition is obtained which comprises glucose, sucrose, the trisaccharide ($GF_2$), the tetrasaccharide ($GF_3$) as well as minor amounts of fructose, pentasaccharide ($GF_4$) and hexasaccharide ($GF_5$). The amount of higher inulins drops off dramatically, the majority fraction being inulin $GF_{2-3}$.

Kono et al. U.S. Pat. No. 5,314,810 report that the half-life of an immobilized fructosyltransferase used in the reaction of sucrose can be improved by support on a granular carrier such as chitosan derivative or an anion exchange resin. Such a supported enzyme is reported to allow for the industrial production of a low cariogenic sweetener composition.

Heady U.S. Pat. No. 4,317,880 reports the production of novel fructose polymers and high fructose syrups from sucrose by the combined action of a fructosyl transferase enzyme and a glucose isomerase enzyme preparation.

Heady U.S. Pat. No. 4,335,207 reports a two step process for the preparation of fructose polymers and ethyl alcohol from sucrose by contacting with a fructosyl transferase enzyme followed by fermentation with a yeast preparation.

Present methods for preparation of glucose and fructose from sucrose however, have suffered from poor efficiency, such that the production of commercial quantities of glucose and fructose can be improved.

In addition, there remains a need for processes for preparing commercial quantities of polysaccharides such as inulins and in particular $GF_{4-5}$ and polyglucans such as polydextrose substitutes, cellulose, starch, and those which may be used for the treatment of dental caries.

SUMMARY OF THE INVENTION

It is an object of the present invention to provide a process for preparing commercial quantities of glucose and/or fructose from sucrose.

It is another object to provide a process for preparing commercial quantities of the glucose and a polyfructan from sucrose.

It is another object to provide a process for preparing commercial quantities of the fructose and a polyglucan from sucrose.

These and other objects may be accomplished with a process for preparing commercial quantities of glucose and/or fructose comprising contacting sucrose with a fructosyltransferase and/or a glucosyltransferase in a reactor and isolating commercial quantities of glucose and/or fructose therefrom.

The objects above may also be accomplished with a process for preparing commercial quantities of glucose, by contacting sucrose with a fructosyltransferase in a reactor to produce a reaction product comprising glucose and a polyfructan, followed by isolating commercial quantities of glucose.

The objects above may also be accomplished with a process for preparing commercial quantities of fructose, by contacting sucrose with a glucosyltransferase in a reactor to produce a reaction product comprising fructose and a polyglucan, followed by isolating commercial quantities of fructose.

The present invention is based, in-part, on the discovery that fructosyltransferases can be used to prepare commercial quantities of glucose from sucrose (GF) and that glucosyltransferases can be used to prepare commercial quantities of fructose from sucrose (GF). In addition, polyfructans produced during the formation of glucose by the reaction of sucrose and a fructosyltransferase and polyglucans produced during the formation of fructose by the reaction of sucrose with a glucosyltransferase may be isolated in commercial quantities to further enhance the economic value of the present process.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
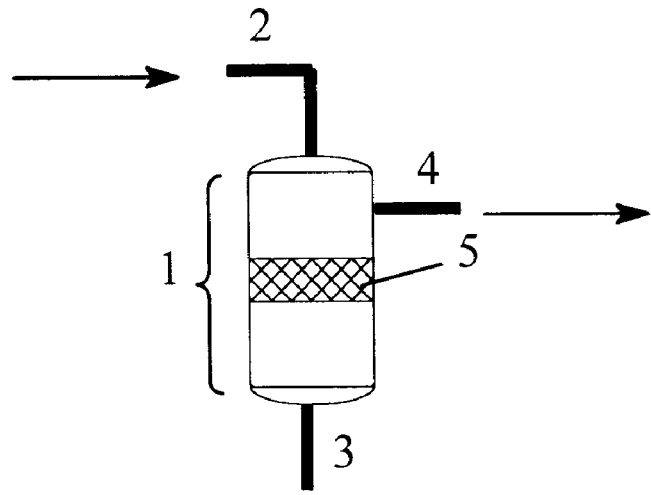
FIG. 1 depicts a flow diagram in which sucrose is converted to glucose and a polyfructan.

Glucose is a staple article of commerce and is sold for pharmaceutical and food uses. Fructose is a staple article of commerce and is sold for pharmaceutical and food uses. $GF_{4-5}$ has utility as a bulking agent for food compositions. When used in combination with a sweetener, a sweetening composition having sugar-like volume and texture may be obtained. $GF_{4-5}$ has little or no sweetness. Polyglucans comprised of $\alpha$-1,3 and $\alpha$-1,6 linkages may be useful for the treatment and prevention of dental caries. A synthetic $\beta$-1,4 polyglucan is a source of high purity cellulose which may be used to manufacture high quality paper. A synthetic polyglucan comprised of from 5 to 11 glucose units, comprised of more than one type of glycosidic linkage and including branching linkages, may be used as a bulking agent for food as a substitute for polydextrose. Accordingly methods and apparatuses for the preparation of glucose, fructose, polyfructans and polyglucans have utility.

As used herein, the term "fructosyltransferase" refers to any enzyme or enzymes capable of transferring fructose moieties to sucrose or to another saccharide (e.g. a polyfructan). A result of transferring the fructose moiety of sucrose is the production of a glucose unit. In a preferred embodiment, the fructosyltransferase transfers the fructose moiety of sucrose and forms $\beta$-2,1 linkages, so as to produce inulins such as $GF_{4-5}$ from sucrose.

Non-limiting examples of suitable fructosyltransferases may be obtained from microorganisms of the genus Aspergilus such as A. oryzae ATCC 20498; A. sp. ATCC 20524; A. awamori, A. sydowi and A. niger ATCC 20611 from the genus Penicillium such as P. jancezewskii ATCC 10115 and 26546; P. nigricans, from the genus Fusarium such as F. lini IAM 5011; and from the genus Aureobasidium such as A. pullulans ACTT 9348; Streptococcus mutans ATCC 25175; and A. pullulans var. melanigenum A-8 ATCC 20612. Suitable enzymes may also be obtained from yeasts and other microorganisms such as the genus Saccharomyuces, such as S. cerevisiae, the genus Rhodotorula such as R. lutinis, the genus Pichia such as P. miso, the genus Hansenula such as H. miso, the genus Candida such as C. tropicalis, and from higher plants such as asparagus, dahlia tubers, chicory roots and the Jerusalem artichoke as described in JP-A-56-154967 and JP-B-59-53834. Another fructosyltransferase (also known as a levan synthetase) having a β-2,6 linkage forming activity, may also be used. A combination of fructosyltransferases having both β-2,1 and β-2,6 linkage forming activity may be used together, to form either a polyfructan having a homogenous distribution of β-2,1 and β-2,6 linkages or blocks comprising β-2,1 linkages and blocks comprising β-2,6 linkages.

One particularly preferred enzyme is a bacterial fructosyltransferase which may be obtained from a gene isolated from *Streptococcus mutans*. In particular *S. mutans* ATCC 25175; may be a source of a fructosyltransferase gene. The fructosyltransferase may be obtained as a fusion construct with a heterologous protein sequence. A suitable fusion protein is, for example, the fructosyltransferase isolated from *Streptococcus mutans* fused to the C-terminal of glutathione-S-transferase.

The coding sequence of the *Streptococcus mutans* frucotosyltransferase, lacking the predicted signal sequence may be isolated from *Streptococcus mutans* strain ATCC 25175 by PCR which may be used to form a transformant which expresses a fructosyltransferase fusion protein. Another suitable fructosyltransferase gene sequence from *Streptococcus mutans* strain GS-5 is reported by Shiroza, T. and Kuramitsu, H. K. *J. Bacteriol.*, 170, 810–816 (1988).

The fructosyltransferase may be immobilized on a carrier having a primary to quaternary amine as described in U.S. Pat. No. 5,314,810.

In a preferred embodiment, the fructosyltransferase is at least partially purified. As used herein the term "purified" means that the enzyme has been purified, at least partially from the host organism from which it was produced naturally. Purification preferably results in at least partial removal of degradative enzymes such as inulases which would degrade the polyfructan and proteases which may degrade the fructosyltransferase enzyme. Preferably the enzyme is purified to a degree such that there is the absence of degradative enzymes. When the source of the enzyme is a transfected *E. coli* microorganism, a crude cell lysate may be used, when the transfected *E. coli* has no native degradative enzymes.

In a preferred embodiment, the purified fructosyltransfease has a ratio of synthetic to degradation activity of ≧1,000 to 1, more preferably ≧1,500 to 1 and even more preferably ≧2,000 to 1 (e.g. for every cleavage of a polyfructan linkage, there are preferably at least 1,000 linkages of fructose formed). Where one unit equals one μmole of monsaccharide transferred to an acceptor per minute, a crude *A. niger* growth supernatant contains ~90 units/mg protein, and a DEAE-purified *A. niger* preparation has ~2,000 units/mg protein. 250 milliliters of DEAE-purified preparation has sufficient activity to convert completely one liter of 50% sucrose to glucose and a polyfructan in about 2.5 days at 50° C. Alternatively, the same enzyme preparation may operate continuously, and with no drop in efficiency, for at least two weeks at 50° C., while sucrose is continually added.

The fructosyltransferase may be purified to an activity of from 90 to 3,000 U/mg, preferably from 100 to 2,000 U/mg. In a preferred embodiment, the frucotsyltransfease will have an activity of ≧100 U/mg, preferably ≧150 U/mg, even more preferably ≧200 U/mg.

As used herein, the term "glucosyltransferase" refers to any enzyme or enzymes capable of transferring glucose moieties to glucose or to another saccharide (e.g a polyglucan). The glucosyltransferase may comprise a plurality of enzymes capable of transferring glucose moieties, providing for a polyglucan having more than one type of linkage. In one embodiment, the glucosyltransferase transfers the glucose moiety of sucrose to form a polyglucan. A result of transferring the glucose moiety of sucrose is the production of a fructose unit. In a preferred embodiment, the glucosyltransferase forms α-1,3 and/or α-1,6 linkages, so as to produce polyglucans which may be used to treat dental caries. In another preferred embodiment, the glucosyltransferase forms a plurality of linear and branched linkages, so as to produce a polydextrose substitute. In another preferred embodiment, the glucosyltransferase forms β-1,4 linkages, so as to produce celluose. In another preferred embodiment, the glucosyltransferase forms β-1,3 linkages, so as to produce callose. In another preferred embodiment, the glucosyltransferase forms α-1,4 or α-1,6 linkages, so as to produce starches. In another preferred embodiment, a mixture of glucosyltransferases forms both α-1,4 and α-1,6 linkages, so as to produce starches.

Suitable glucosyltransfeases may be obtained by conventional means known to those of ordinary skill in the art. For example, glucosyltransferases are described by J. F. Robyt in *Adv Carbohydr. Chem. Biochem.* 1995, 51:133–168. The cloning of a plant cellulose synthase is described by J. R. Pear et al. *Proc. Natl. Acad. Sci. U.S.A.* (1996) 93, (22), 12637–12642. The isolation of a plant callose synthase is described by Kamat et al. *Arch biochem. Biophys,* 298(2) :731–739 and by Kudlicka and Brown *Plant Physiol* (1997) 115(2):643–656. The cloning of *Streptococcus mutans* synthetase is reported by Ueda et al. *Gene* (1988) 69, (1) 101–109, by Shiroza et al. *J. Bacteriol.* (1987) (9), 4263–4270 and by Honda et al. *J. Gen. Microbiol.* (1990) 136, 2099–2105. The cloning of a bacterial glycogen (amylase) is described by Buttcher et al. *J. Bacteriol.* (1997) 179 (10) 33244–3330.

Non-limiting examples of suitable glucosyltransferases may also be obtained from *Streptococcus mutans* as disclosed in U.S. Pat. No. 4,438,200 and *Pullularia pullulans* as disclosed in U.S. Pat. No. 4,774,183.

The glucosyltransferase may be immobilized on a carrier having a primary to quaternary amine in a manner analogous to that described in U.S. Pat. No. 5,314,810.

In a preferred embodiment, the glucosyltransferase is at least partially purified. As used herein the term "purified" means that the enzyme has been purified, at least partially from the host organism from which it was produced naturally. Purification preferably results in the at least partial removal of degradative enzymes such as amylases which would degrade the polyglucan and proteases which may degrade the glucosyltransferase enzyme. Preferably the enzyme is purified to a degree such that there is the absence of degradative enzymes. When the source of the enzyme is a transfected *E. coli* microorganism, a crude cell lysate may be used, when the transfected *E. coli* has no native degradative enzymes.

In a preferred embodiment, the purified glucosyltransfease has a ratio of synthetic to degradation activity of ≧1,000 to 1, more preferably ≧1,500 to 1 and even more preferably ≧2,000 to 1 (e.g. for every cleavage of a polyglucan linkage, there are preferably at least 1,000 linkages of glucose formed).

The glucosyltransferase may be purified to an activity of from 90 to 3,000 U/mg, preferably from 100 to 2,000 U/mg. In a preferred embodiment, the glucosyltransfease will have an activity of ≧100 U/mg, preferably ≧150 U/mg, even more preferably ≧200 U/mg.

The starting material for the present process will be sucrose or a sucrose containing composition. Sucrose refers to the disaccharide in refined or raw form, as a solution or dry, from any sucrose raw material source, e.g. sugar cane, or sugar beets. Preferably the amount of sucrose contained in the sucrose raw material is $\geq 10$ wt. %, more preferably $\geq 20$ wt. %, even more preferably $\geq 50$ wt. %, most preferably $\geq 70$ wt. %. The feed stock may contain other materials so long as they do not significantly interfere with the conversion of sucrose to glucose and/or fructose.

Sucrose may be introduced in any of the forms as described above. In order to maintain the overall ionic strength and concentration of the reaction medium however, sucrose is continuously or intermittently introduced in dry form or in solution. The rate and frequency of sucrose addition to the reaction mixture will be such as to maintain a high rate of production of polysaccharide and will in part depend on the nature and specific activity of the transferase enzyme, the reaction temperature and whether or not removal of glucose and polyfructan is performed. The determination of the optimum rate and frequency of sucrose addition can be accomplished by routine experimentation and is within the level of skill of those of ordinary skill in the art.

The process of the present invention is preferably conducted in aqueous solution.

The concentration of sucrose in the reaction medium is not particularly limited and may be 50 mM up to saturation. In terms of weight percent, the amount of sucrose in the reaction solution may be 1 to 80% by weight, based on the total weight of the reaction mixture, typically from 40 to 80% w/w, preferably from 50 to 70% w/w and more preferably about 60% w/w.

In order to obtain efficient conversion of sucrose to the desired monosacccharide, it is preferable to conduct the reaction in at least two stages, initiating the reaction of the transferase with sucrose using approximately 50 wt. % of sucrose.

For example, when a fructosyltransfease is being used to form glucose, the initial reaction of sucrose with the fructosyltranserase will produce a reaction mixture comprising primarily glucose, and lower polyfructans such as $GF_2$ and $GF_3$. At this stage the glucose is preferably removed by conventional methods known to those of ordinary skill in the art. The reaction mixture comprising primarily polyfructans and optionally glucose is then contacted with the fructosyltransferase and additional sucrose. During the second addition of sucrose, most of the sucrose molecules will be is reacted with the polyfructans so as to produce glucose and higher polyfructan, as opposed to the sucrose molecules acting as a receptor for a transfer of fructose. In the production of $GF_2$ one mole of glucose is formed from two moles of sucrose, while in forming the higher polyfructans, glucose is produced more efficiently, illustrated as follows:

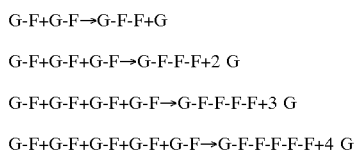

When $GF_2$ is produced from two moles of sucrose, only about 25 wt. % of sucrose is recovered as glucose. When $GF_3$ is produced from three moles of sucrose, about 33 wt. % of sucrose is recovered as glucose. For $GF_4$ the recovery as glucose is about 37 wt. %, for $GF_5$ about 40 wt. % and for $GF_6$ about 41.6 wt. %. Accordingly, by practicing a two stage reaction, high yield of glucose (>25 wt. % based on reacted sucrose) can be obtained, providing for the commercial synthesis of glucose.

The polyfructans $GF_2$ and $GF_3$ are comprised of three and four monosaccharide units respectively, and accordingly, may be generically be referred to as $DP_3$ and $DP_4$, indicating the number of monosaccharide units, independent of their identity. Higher polyfructans may also be identified by the number of monosaccharide units, e.g. $DP_5$, $DP_6$ and $DP_7$ corresponding to $GF_4$, $GF_5$ and $GF_6$ respectively. Likewise polyglucans may be identified by the number of monosaccharide unite contained therein, such as $DP_3$, $DP_4$, $DP_5$, and $DP_6$ for polyglucans containing three, four, five and six monosaccharide units respectively.

In an analogous manner the synthesis of fructose from sucrose under the action of a glucosyltransferase may be effected in at least two stages.

The reaction of sucrose with fructosyltransferase or glucosyltransferase may be conducted over a wide temperature range. The reaction temperature may be room temperature, i.e. 18 to 25° C., up to temperatures just below the temperature where rapid inactivation of the fructosyltransferase or glucosyltransferase occurs. A preferred temperature range is 25 to 60° C. More preferably, the reaction is conducted at a temperature of 35 to 55° C. Most preferably, the temperature is 30 to 50° C.

The aqueous reaction solutions may be unbuffered or buffered at the appropriate pH using well-known buffer components, such as citrate, phosphate, and TRIS buffers. The use of a buffer is preferred when the reaction is conducted for an extended period of time, such as two weeks.

The reaction of sucrose with fructosyltransferase or glucosyltransferase is conducted for a time sufficient to produce commercial quantities of glucose and/or fructose. The reaction time may be 2 to 48 days, depending on the size of the batch. When conducted on in a continuous manner, a 10 mL volume may react at a rate of 2.5 g/hr, without a significant lose of activity, for a period of from 2 to 4 weeks.

The pH of the reaction of sucrose with fructosyltransferase or glucosyltransferase is not particularly limited and the optimum pH of the reaction may vary depending on the specific enzyme used. Typically the pH will be from 4.0 to 8.0, preferably from 5.0 to 7.5, more preferably about 6.0.

The present process may be conducted in either a batchwise or continuous mode. The continuous reaction may be conducted by circulating a reaction mixture through an ultrafiltration apparatus whereby the product(s) are continually removed as the permeates from ultrafilters, a transferase enzyme being retained in the retentate from the ultrafilters. Fresh substrate and fresh enzyme may be added, as needed, to replace those that have become inactivated, addition to the reaction mixture being at the same rate in which the permeates are removed from the ultrafilters.

The reaction may be conducted in a reactor or series of reactors, which may also be equipped with suitable inlet reactants and outlets for products. The outlets may be selective for the removal of a specific product. Selectivity may be obtained by providing suitable separators which permit the removal of product and return of other materials to the reactor. A separator may be in the form of a membrane or a chromatography column. In some cases, a separator may comprise a plurality of membranes and/or chromatography columns providing for the selective removal of the desired product.

After the reaction to produce glucose and/or fructose the fructosyltransferase and/or glucosyltransferase may be inactivated by heating a reaction mixture to about 100° C. for from 10 to 15 minutes. If desired, the enzyme may be removed from the reaction mixture either before or after heat inactivation by means of ultrafiltration through a filter of suitable size.

For the purposes of illustration specific details are provided for the preparation of glucose from sucrose using a fructosyltransferase. It will be appreciated by those of ordinary skill in the art that in an analogous fashion fructose maybe prepared from glucose by the action of a glucosyltransferase.

Sucrose and a fructosyltransferase are reacted in a reactor. The reactor may comprise an inlet for sucrose and an outlet of glucose. As the degree of polymerization increases, the concentration of glucose will also increase such that it is possible that the rate of glucose forming reaction will decrease. Accordingly in a preferred embodiment, glucose is removed from the reaction medium, during the reaction. The glucose may be removed by conventional methods known to those of ordinary skill in the art such as by membrane filtration or chromatography. Within the context of the present invention, chromatography includes ion exchange and gel exclusion techniques, known to those of ordinary skill in the art. A pump may be used to increase the pressure against the membrane or chromatography column. In a preferred embodiment, the outlet for glucose comprises a membrane which permits the flow of glucose from the reaction medium, without allowing sucrose, polyfructan or fructosyltransferase to pass through.

Glucose may be removed continuously, batchwise or semibatchwise, however, in a preferred embodiment, glucose is removed continuously from the reaction medium.

The glucose may be isolated and purified by conventional methods known to those of ordinary skill in the art such as by filtration which may also be followed by crystallization.

In a preferred embodiment, the polyfructan is also removed from the reaction mixture, more preferably, the polyfructan is removed continuously from the reaction mixture. A polyfructan may be removed by conventional methods known to those of ordinary skill in the art such as by membrane filtration or chromatography, such as ion exchange or gel exclusion. In a preferred embodiment, an outlet for polyfructan comprises a membrane which permits the flow of polyfructan from the reaction medium, without allowing sucrose, glucose or fructosyltransferase to pass through. Alternatively, the polyfructan may be separated from the reaction mixture, returning sucrose and glucose to the reaction mixture.

In a preferred embodiment the amount of polyfructan produced, based on the starting weight of sucrose is $\geq 10$ wt. %, preferably $\geq 20$ wt. %, even more preferably $\geq 30$ wt. %, even more preferably $\geq 40$ wt. %, and most preferably $\geq 50$ wt. %.

In a preferred embodiment the yield of glucose produced, based on the reacted weight of sucrose, is from 25 to 50 wt. % preferably $\geq 25$ wt. %, preferably $\geq 33$ wt. %, even more preferably $\geq 37$ wt. %, even more preferably $\geq 40$ wt. %, and most preferably about 50 wt. %.

Within the context of the present invention, commercial quantities are defined as a rate of production of glucose of from $10^3$ to $10^5$ kg/day and will preferably be an amount of $\geq 1,000$ kg/day, preferably $\geq 2,000$ kg/day, even more preferably $\geq 5,000$ kg/day. In addition, the rate of production of commercial quantities is relative to the amount of sucrose starting material. Therefore the above identified rates of production are based on a unit processing of 6,000 kg of sucrose. Accordingly the term "commercial quantities" does not refer to an absolute amount, but rather refers to a commercially acceptable rate of production.

Now referring to FIG. 1, where 1 depicts a reactor, 2 depicts an inlet for sucrose, 3 depicts a outlet for glucose, 4 depicts an outlet for a polyfructan and 5 depicts a separator which is permeable to glucose but not permeable to, sucrose, a fructosyltransferase or a polyfructan. Sucrose is introduced to the reactor via inlet 2 to a portion of reactor 1 which contains a fructosyltransferase. In such a configuration, a partition is created such that polyfructans are concentrated on one side of the separator. The reactor is equipped with a glucose outlet 3, located on the glucose side of the separator 5. The outlet for polyfructan 4, may be equipped with a separator (not shown) which permits the passage of polyfructan, but does not permit passage of sucrose, glucose or fructosyltansferase.

Figure 1A:
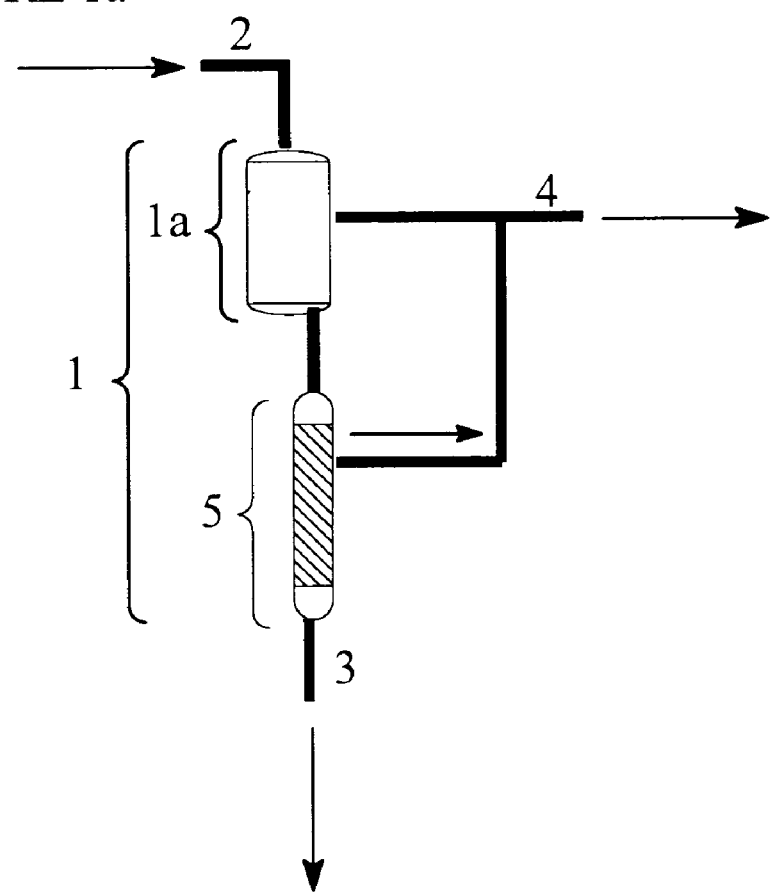
FIG. 1a depicts a flow diagram in which sucrose is converted to glucose and a polyfructan in a reactor vessel equipped with an external separator for glucose.

Now referring to FIG. 1a, where 1 depicts a reactor, 1a depicts a separate reactor portion, 2 depicts an inlet for sucrose, 3 depicts a outlet for glucose, 4 depicts an outlet for a polyfructan and 5 depicts a separator for glucose. Sucrose is introduced to the reactor via inlet 2 to a reactor portion 1a of reactor 1, which contains a fructosyltransferase. In such a configuration, glucose is separated from the reaction medium by separator 5, before being removed via glucose outlet 3. During the separation of glucose, the remaining materials may be recycled to reactor portion 1a. The outlet for polyfructan 4, may be equipped with a separator (not shown) which permits the passage of polyfructan, but does not permit passage of sucrose, glucose or fructosyltransferase.

In another embodiment, a reactor comprising an inlet for sucrose is equipped with an external separator, which separates both glucose and a polyfructan from sucrose. Unreacted sucrose, if any, may be returned to the reactor.

Figure 2:
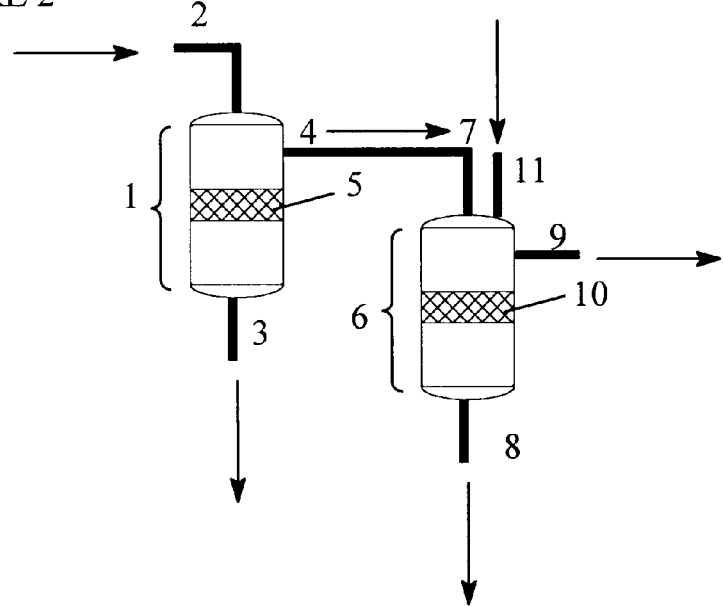
FIG. 2 depicts a flow diagram in which sucrose is converted to glucose and a polyfructan in two reaction vessels.

Now referring to FIG. 2, where 1 depicts a first reactor, 2 and 11 depict inlets for sucrose, 3 and 8 depict outlets for glucose, 4 depicts an outlet for a $GF_{2-3}$ or higher polyfructan, 5 and 10 depict separators which are permeable to glucose but not permeable to sucrose, a fructosyltransferase or a polyfructan, 6 depicts a second reactor, 7 depicts an inlet for a $GF_{2-3}$ polyfructan and 9 depicts an outlet for a $GF_{4-5}$ or higher polyfructan. Two reactors are used, each partitioned with separators 5 and 10 which are permeable to glucose but impermeable to sucrose, a fructosyltransferase or to polyfrucans of $GF_2$ and higher. In the first reactor 1, the concentration of sucrose is such as to provide for the synthesis of $GF_2$, the product then being transferred to the second reactor 6 via inlet for a $GF_{2-3}$ or higher polyfructan. In the second reactor 6, a fructosyltransferase is contained in a portion of a second reactor 6 and a $GF_{2-3}$ or higher polyfructan is reacted with sucrose, wherein the concentration of sucrose is lower than in the first reactor 1. The concentration of sucrose is maintained at a desired level by introduction of sucrose via inlet 11. The low concentration of sucrose favors the synthesis of higher polyfructans and accordingly, the effective synthesis of glucose. Glucose is permitted to pass through separator 10 and is removed via glucose outlet 8. During the separation of glucose, the remaining materials may be recycled to reactor portion 6. The higher polyfructan may be removed via polyfructan outlet 9. The outlet for polyfructan 9, may be equipped with a separator (not shown) which permits the passage of polyfructan, but does not permit passage of sucrose, glucose or fructosyltransferase.

Figure 2A:
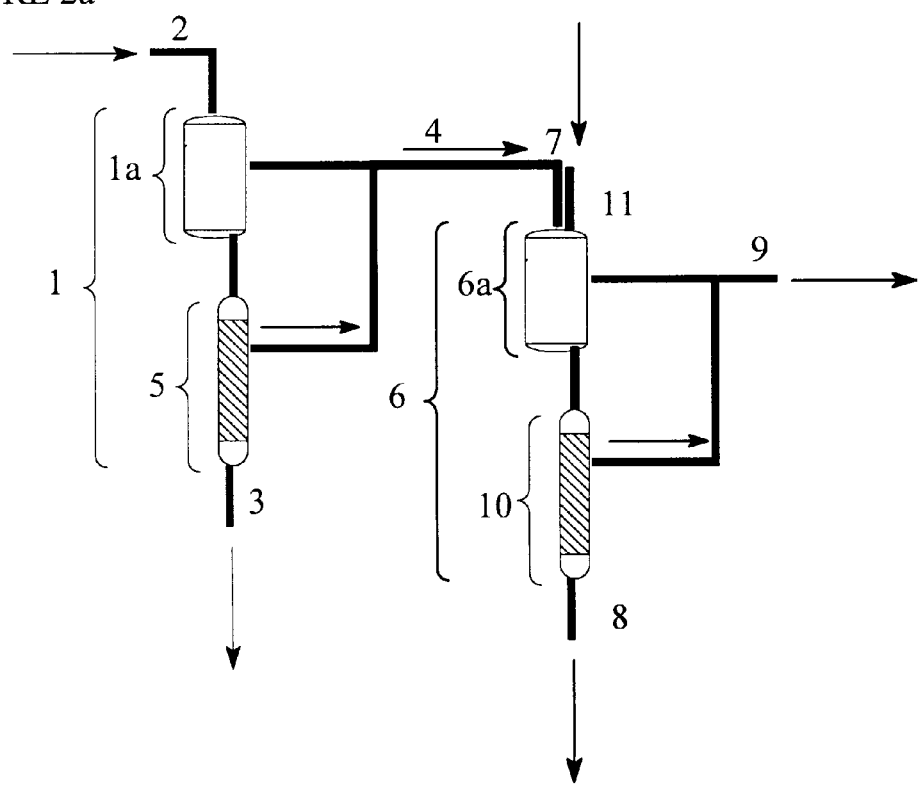
FIG. 2a depicts a flow diagram in which sucrose is converted to glucose and a polyfructan in two reaction vessels, each equipped with external separators for glucose.

Now referring to FIG. 2a, where 1 depicts a first reactor and 1a depicts a separate reactor portion, 2 and 11 depict inlets for sucrose, 3 and 8 depict outlets for glucose, 4 depicts an outlet for a $GF_{2-3}$ or higher polyfructan, 5 and 10 depict external separators which are permeable to glucose but not permeable to sucrose, a fructosyltransferase or a polyfructan, 6 depicts a second reactor and 6a depicts a separate reactor portion, 7 depicts an inlet for a $GF_{2-3}$ polyfructan and 9 depicts an outlet for a $GF_{4-5}$ or higher polyfructan. Two reactors are used, equipped with external separators 5 and 10 which are permeable to glucose but impermeable to sucrose, a fructosyltransferase or to polyfrucans of $GF_2$ and higher. In the first reactor portion 1a, the concentration of sucrose is such as to provide for the synthesis of $GF_2$, the product then being transferred to the second separate reactor portion 6a via inlet for a $GF_{2-3}$ or higher polyfructan 7. In the second reactor 6, a fructosyltransferase is contained in separate reactor portion 6a and a $GF_{2-3}$ or higher polyfructan is reacted with sucrose, wherein the concentration of sucrose is lower than in the first reactor 1. The concentration of sucrose is maintained at a desired level by introduction of sucrose via inlet 11. The low concentration of sucrose favors the synthesis of higher polyfructans and accordingly, the effective synthesis of glucose. Glucose is permitted to pass through separator 10 and is removed via glucose outlet 8. The higher polyfructan may be removed via polyfructan outlet 9. The outlet for polyfructan 9, may be equipped with a separator (not shown) which permits the passage of polyfructan, but does not permit passage of sucrose, glucose or fructosyltransferase. Both separators 5 and 10 are depicted with a recycle line to return materials other than glucose such as sucrose and polyfrucan if necessary.

The process of the present invention is preferably conducted in a reactor suitable for making commercial quantities of $GF_{4-5}$. Preferably the reactor comprises one or more inlets for introducing sucrose and/or the fructosyltransferase and a means for isolating commercial quantities of $GF_{4-5}$ from the reactor. The reactor may comprise multiple vessels, as illustrated in FIGS. 2 and 2a, functioning as a reactor system.

Details of a process of preparing fructose from sucrose will now be described.

Sucrose and a glucosyltransferase are reacted in a reactor. The reactor may comprise an inlet for sucrose and an outlet for fructose. As the degree of polymerization increases, the concentration of fructose will also increase such that it is possible that the rate of fructose forming reaction will decrease. Accordingly in a preferred embodiment, fructose is removed from the reaction medium, during the reaction. The fructose may be removed by conventional methods known to those of ordinary skill in the art such as by membrane filtration or chromatography such as ion exchange and gel exclusion techniques. A pump may be included in the system to increase the pressure of fluid against the separator. In a preferred embodiment, the outlet for fructose comprises a membrane which permits the flow of fructose from the reaction medium, without allowing sucrose, polyglucan or glucosyltransferase to pass through.

Fructose may be removed continuously, batchwise or semibatchwise. However, in a preferred embodiment, fructose is removed continuously from the reaction medium.

The fructose may be isolated and purified by conventional methods known to those of ordinary skill in the art, such as by filtration, by chromatography, or by crystallization.

In a preferred embodiment, the polyglucan is also removed from the reaction mixture. In an even more preferred embodiment, the polyglucan is removed continuously from the reaction mixture. A polyglucan may be removed by conventional methods known to those of ordinary skill in the art such as by membrane filtration or chromatography such as ion exchange or gel exclusion. In a preferred embodiment, an outlet for polyglucan comprises a membrane which permits the flow of polyglucan from the reaction medium, without allowing sucrose, fructose or glucosyltransferase to pass through.

In a preferred embodiment the amount of polyglucan produced, based on the starting weight of sucrose is $\geq 10$ wt. %, preferably $\geq 20$ wt. %, even more preferably $\geq 30$ wt. %, even more preferably $\geq 40$ wt. %, and most preferably $\geq 50$ wt. %.

In a preferred embodiment the yield of fructose produced, based on the reacted weight of sucrose, is from 25 to 50 wt. % preferably $\geq 25$ wt. %, preferably $\geq 33$ wt. %, even more preferably $\geq 37$ wt. %, even more preferably $\geq 40$ wt. %, and most preferably about 50 wt. %.

Within the context of the present invention, commercial quantities are defined as a rate of production of fructose of from $10^3$ to $10^5$ kg/day and will preferably be an amount of $\geq 1,000$ kg/day, preferably $\geq 2,000$ kg/day, even more preferably $\geq 5,000$ kg/day. In addition, the rate of production of commercial quantities is relative to the amount of sucrose starting material. Therefore the above identified rates of production are based on a unit processing of 6,000 kg of sucrose. Accordingly the term "commercial quantities" does not refer to an absolute amount, but rather refers to a commercially acceptable rate of production.

Figure 3:
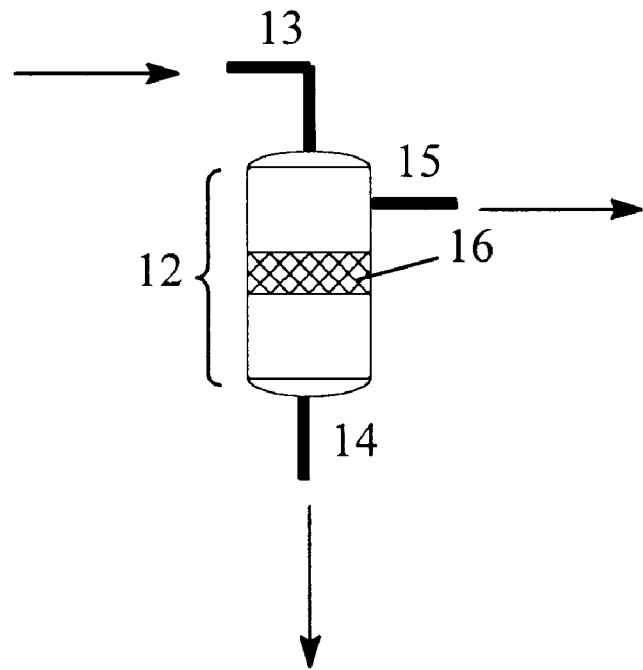
FIG. 3 depicts a flow diagram in which sucrose is converted to fructose and a polyglucan.

Now referring to FIG. 3, where 12 depicts a reactor, 13 depicts an inlet for sucrose, 14 depicts a outlet for fructose, 15 depicts an outlet for a polyglucan and 16 depicts a separator which is permeable to fructose but not permeable to, sucrose, a glucosyltransferase or a polyglucan. Sucrose is introduced to the reactor via inlet 13 to a portion of reactor 12 which contains a glucosyltransferase. In such a configuration, a partition is created such that polyglucans are concentrated on one side of the separator. The reactor is equipped with a fructose outlet 14, located on the fructose side of the separator 16. The outlet for polyglucan 15, may be equipped with a separator (not shown) which permits the passage of polyglucan, but does not permit passage of sucrose, fructose or glucosyltransferase.

Figure 4:
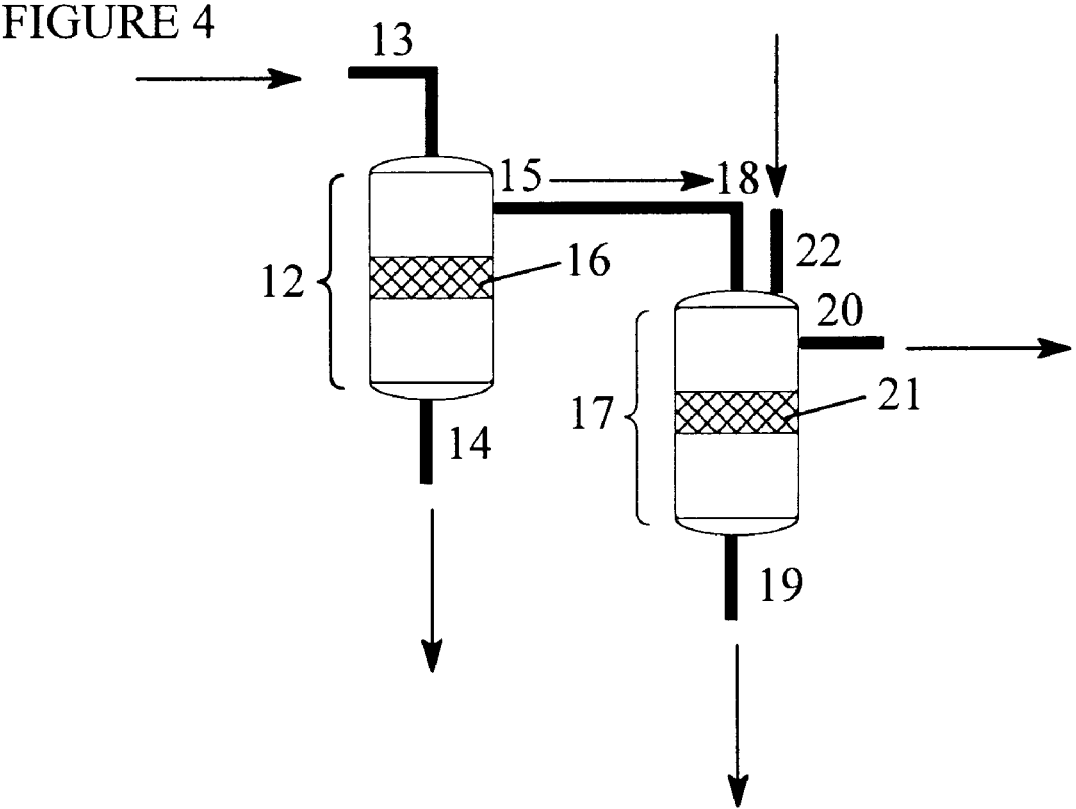
FIG. 4 depicts a flow diagram in which sucrose is converted to fructose and a polyglucan in two reaction vessels.

Now referring to FIG. 4, where 12 depicts a first reactor, 13 and 22 depict inlets for sucrose, 14 and 19 depict outlets for fructose, 15 depicts an outlet for a $DP_{3-4}$ or higher polyglucan, 16 and 21 depict separators which are permeable to fructose but not permeable to sucrose, a glucosyltransferase or a polyglucan, 17 depicts a second reactor, 18 depicts an inlet for a $DP_{3-4}$ or higher polyglucan and 20 depicts an outlet for a $DP_{5-6}$ or higher polyglucan. Two reactors are used, each partitioned with separators 16 and 21 which are permeable to fructose but impermeable to sucrose, a glucosyltransferase or to polyglucans of $DP_3$ and higher. In the first reactor 12, the concentration of sucrose is such as to provide for the synthesis of $DP_3$, the product then being transferred to the second reactor 6 via inlet for a $DP_{3-4}$ polyglucan 18. In the second reactor 17, a glucosyltransferase is contained in a portion of second reactor 17 and a $DP_{3-4}$ or higher polyglucan is reacted with sucrose, wherein the concentration of sucrose is lower than in the first reactor 12. The concentration of sucrose is maintained at a desired level by introduction of sucrose via inlet 22. The low concentration of sucrose favors the synthesis of higher polyglucans and accordingly, the effective synthesis of fructose. Fructose is permitted to pass through separator 21 and is removed via fructose outlet 19. The higher polyglucan may be removed via polyglucan outlet 20.

It is also within the scope of the present invention to conduct additional modifications of the enzymatically produced polyfructan or polyglucan, by either conventional chemical modification or additional enzymatic modification. Non-limiting examples of chemical modification may include alkylation, esterification, dehydration, cyclization and partial hydrolysis. Non-limiting examples of enzymatic modification may include glycosylation.

Figure 5:
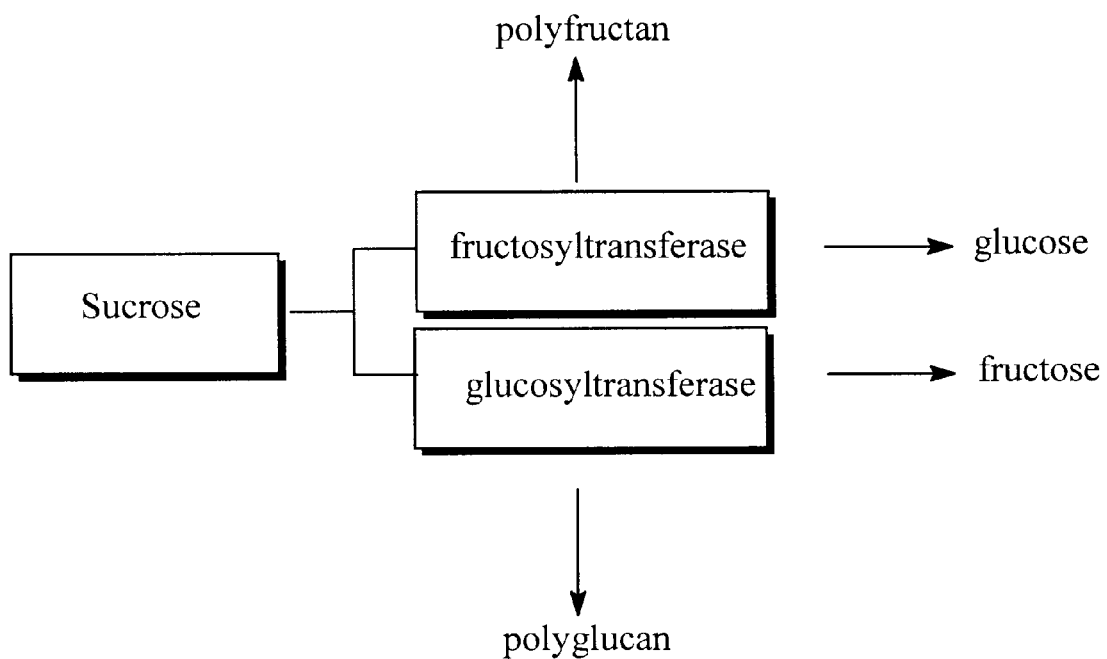
FIG. 5 depicts a schematic diagram of an integrated process for producing glucose and fructose from sucrose.

The present process also provides for an integrated process for producing both glucose and fructose from sucrose by the action of both a fructosyltransferase and a glucosyltransferase. In such a process a sucrose feed stream is provided to separate reactors containing a fructosyltransferase and a glucosyltransferase. The individual reactors separately provide for production of glucose and fructose respectively. A flow diagram of such a process is provided in FIG. 5. The reactors containing the fructosyltransferase and glucosyltransferase may be as described above or as illustrated in FIGS. 1, 1a, 2, 2a 3, and 4.

The present process and apparatus also provides tremendous flexibility, in the production of glucose and a polyfructan and/or fructose and a polyglucan, from sucrose, the identity and relative amounts of monosaccharide to polysaccharide being freely adjustable depending on the specific enzyme being used and the selected reaction conditions. For example, the relative ratio of glucose to polyfructan may be adjusted by changing the concentration of sucrose, the time of reaction or the number of enzyme units. Increasing the sucrose concentration favors the production of low molecular weight polyfructans, decreasing the sucrose concentration, increasing the reaction time and increasing the number of enzyme units favors the production of higher molecular weight polyfructans and glucose. The specific polysaccharide may also be changed to meet demands, simply by changing the enzyme being used. Accordingly the present process may be quickly adapted to meet changing demands for specific monosaccharides and polysaccharides, without the need to make significant changes to the apparatus.

A polyglucan may be used to treat dental caries by administration to the oral cavity. The water-soluble polyglucan will preferably have a linear or branched structure comprising β-1,3 linked glucose residues, β-1,6 linked glucose residues, or a combination of β-1,3 linked and β-1,6 linked glucose residues. The molecular weight of the polyglucan will preferably be from 1,000 to 1,000,000 daltons.

The anti caries polyglucan may be administered by conventional techniques known to those of ordinary skill in the art for delivery of an agent to the oral cavity. For example a composition comprising the polyglucan may be administered in a mouthwash, a toothpaste or powder, a food, a drink, a chewing gum, a candy, a lozenge, a tablet or in solution.

Suitable amounts of polyglucan are sufficient to maintain an oral concentration of 1 to 1,000 mg/mL, preferably 10 to 500 mg/mL.

The polyglucan comprised of α-1,4 linkages may be used as a synthetic ultrapure cellulose for medical applications. Such an α-1,4 linked polyglucan will preferably have a molecular weight of from 2,000 to 10,000 daltons.

A polyfructan of $GF_{4-5}$ may be used as a bulking agent for foods and food sweeteners.

A polyglucan comprising multiple linkages including branched linkages, comprising from 5 to 11 glucose units may be used as a substituted for polydextrose. Such a polyglucan does not comprise a capping sorbitol unit.

Having generally described this invention, a further understanding can be obtained by reference to certain specific examples which are provided herein for purposes of illustration only and are not intended to be limiting unless otherwise specified.

Cloning and Expression Procedure

The coding sequence of the *Streptococcus mutans* frucotosyltransferase, lacking the predicted signal sequence may be isolated from *Streptococcus mutans* strain ATCC 25175 by PCR. Two primers were designed and synthesized. The first, a 5'-TCTGCGGGATCCCAGGCAGATGAAGCCAATTCAAC-3', contained a BamHI restriction site followed by sequence identical to the sequence immediately following the end of the predicted signal sequence in the *Streptococcus mutans* fructosyltransferase coding sequence. The second, a 5'-TCTGCGAAGCTTTTATTTAAAACCAATGCTTACACA-3', contained a HindIII restriction site followed by the reverse, complement sequence corresponding to the C-terminal end of the *Streptococcus mutans* fructosyltransferase coding sequence. Both primers were combined with genomic DNA isolated from *Streptococcus mutans* strain ATCC 25175 and used in the PCR. The resultant DNA fragment was digested with BamHI and HindIII and ligated to BamHI-HindIII digested plasmid, pGEX-KT-ext. This ligation resulted in the *Streptococcus mutans* fructosyltransferase coding sequence described above, being placed immediately downstream, in frame, with the coding sequence of glutathione-S-transferase (GST). The pGEX-KT-ext-*Streptococcus mutans*-fructosyltransferase plasmid was transformed into *E. coli* BL21 cells. Protein expression from the resultant transformant resulted in intracellular accumulation of a GST-ext *Streptococcus mutans*-fructosyltransferase fusion protein.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing glucose from sucrose comprising:
   i) contacting sucrose with a fructosyltransferase to produce glucose; and
   ii) isolating glucose therefrom
   wherein said reaction product further comprises a polyfructan and said process further comprises isolating said polyfructan.

2. The process of claim 1, wherein said fructosyltransfease is obtained from an organism selected from the group consisting of *Aureobasidium pullulans, Aspergillus oryzae, Aspergillus awamori, Aspergillus sydowi, Aureobasidium sp., Aspergillus niger, Penicillium roquefortii, Streptococcus mutans, Penicillium jancezewskii* and higher plants.

3. The process of claim 1, wherein said frucotosyltransferase is obtained by expression of a non-native fructosyltransferase gene.

4. The process of claim 1, wherein said glucose is isolated continuously or semibatchwise.

5. The process of claim 1, wherein said polyfructan is continuously isolated.

6. The process of claim 1, wherein said glucose is isolated by membrane filtration or chromatography.

7. The process of claim 1, wherein said polyfructan is isolated by membrane filtration or chromatography.

8. A process for preparing commercial quantities of glucose and a polyfructan of comprising:

i) contacting sucrose with a fructosyltransferase to produce a reaction product comprising glucose and a polyfructan; and ii) isolating glucose and said polyfructan.

9. The process of claim 8, wherein said polyfructan is $DP_{5-6}$.

10. The process of claim 9, wherein said glucose is isolated continuously.

11. The process of claim 10, wherein said glucose is isolated continuously by membrane filtration or chromatography.

12. A process of preparing glucose and fructose from sucrose comprising:

i) contacting sucrose with a fructosyltransferase to produce glucose;

ii) contacting sucrose with a glucosyltransferase to produce fructose;

iii) isolating glucose and fructose.

* * * * *